(12) United States Patent
Thakkar

(10) Patent No.: US 8,470,366 B2
(45) Date of Patent: Jun. 25, 2013

(54) NICOTINE CONTAINING SOFT GELATIN PASTILLES

(76) Inventor: Jatin Thakkar, Maharashtra (IN)

(*) Notice: Subject to any disclaimer, the term of this patent is extended or adjusted under 35 U.S.C. 154(b) by 197 days.

(21) Appl. No.: 13/029,163

(22) Filed: Feb. 17, 2011

(65) Prior Publication Data

US 2011/0200670 A1 Aug. 18, 2011

(30) Foreign Application Priority Data

Feb. 18, 2010 (IN) .......................... 452/MUM/2010

(51) Int. Cl.
*A61K 9/20* (2006.01)
*A61K 36/81* (2006.01)
*A61K 31/785* (2006.01)
*A61K 31/44* (2006.01)
*A61K 31/715* (2006.01)

(52) U.S. Cl.
USPC ........ 424/465; 424/751; 424/78.15; 514/343; 514/57; 514/60

(58) Field of Classification Search
USPC ........... 424/465, 751, 78.15, 78, 15; 514/343, 514/57, 60
See application file for complete search history.

(56) References Cited

U.S. PATENT DOCUMENTS

| 4,967,773 | A | 11/1990 | Shaw |
| 5,488,962 | A | 2/1996 | Perfetti |
| 6,110,495 | A * | 8/2000 | Dam ............................ 424/464 |
| 6,183,775 | B1 | 2/2001 | Ventouras |
| 6,280,761 | B1 | 8/2001 | Santus |
| 6,344,222 | B1 | 2/2002 | Cherukuri et al. |
| 2004/0151771 | A1 | 8/2004 | Gin |
| 2005/0002993 | A1 | 1/2005 | Goggin et al. |
| 2005/0034738 | A1 | 2/2005 | Whalen |
| 2005/0053665 | A1 | 3/2005 | Ek et al. |
| 2005/0123502 | A1 | 6/2005 | Chan et al. |
| 2007/0122456 | A1 * | 5/2007 | Lindberg ...................... 424/439 |
| 2007/0202069 | A1 * | 8/2007 | Tamareselvy et al. ..... 424/70.12 |
| 2007/0269386 | A1 | 11/2007 | Steen et al. |
| 2007/0269492 | A1 | 11/2007 | Steen et al. |
| 2010/0004294 | A1 | 1/2010 | Axelsson et al. |

FOREIGN PATENT DOCUMENTS

| GB | 2230439 A | 10/1990 |
| GB | 2299756 A | 10/1996 |
| WO | 2009134947 A1 | 11/2009 |

* cited by examiner

*Primary Examiner* — Blessing Fubara
(74) *Attorney, Agent, or Firm* — Mayback & Hoffman, P.A.; Gregory L. Mayback

(57) ABSTRACT

The present invention relates to soft pastilles for nicotine replacement therapy, said pastille comprises about 0.05% to about 1% of nicotine active; about 5% to about 40% of gelling agent; about 30% to about 70% of plasticizer; about 0.05% to about 10% of sweetener; 0.5% to about 30% of releasing agent; about 0.05% to about 2% of preservative; about 0.01% to 5% of flavoring agent; and about 5% to about 20% of water.

13 Claims, No Drawings

NICOTINE CONTAINING SOFT GELATIN PASTILLES

CROSS-REFERENCE TO RELATED APPLICATIONS

This application claims the priority, under 35 U.S.C. §119, of Indian patent application No. 452/MUM/2010, filed Feb. 18, 2010; the prior application is herewith incorporated by reference in its entirety.

STATEMENT REGARDING FEDERALLY SPONSORED RESEARCH OR DEVELOPMENT

Not applicable.

FIELD OF THE INVENTION

The present invention relates to pastilles.
Particularly, the present invention relates to soft pastilles for nicotine replacement therapy.

BACKGROUND OF THE INVENTION

In the context of the present invention a soft pastille means a resilient preparation which is can be retained and sucked in the mouth.

Nicotine is an alkaloid found in the plants belonging to family Solanaceae. Nicotine is a hygroscopic, oily liquid which is miscible with water in its base form. Nicotine is optically active and has two enantiomeric forms. The naturally occurring form of nicotine is levorotatory. The dextrorotatory form ((+) nicotine) has only one-half the physiological activity of (−) nicotine. It is therefore weaker in the sense that a higher dose is required to attain the same effects. As nicotine enters the body, it is distributed quickly through the bloodstream and can cross the blood-brain barrier. On an average it takes about ten seconds for the substance to reach the brain when inhaled. The half life of nicotine in the body is around two hours.

Nicotine is the main addictive ingredient in the tobacco used in cigarettes, cigars, snuff and other nicotine-containing products. It is generally known that active as well as passive smoking of tobacco products, such as cigarettes, cigars and pipe tobacco presents serious health risks to the user and those subjected to secondary smoke. It is also known that the use of smokeless forms of tobacco, such as chewing tobacco, spit tobacco and snuff tobacco presents serious health risk to the user.

During smoking a cigarette, nicotine is quickly absorbed into the smoker's blood and reaches the brain within ten seconds after inhalation. The quick uptake of nicotine gives the consumer a rapid satisfaction or kick. The poisonous, toxic, carcinogenic and addictive nature of smoking has initiated efforts to search for methods, compositions and devices which would help in breaking the habit of smoking cigarettes.

Smokers and other tobacco users often try to quit the potentially deadly habit. Although the damaging effects of tobacco usage are well known, most individuals who are nicotine dependent have great difficulty in overcoming their dependence on nicotine. The difficulty arises in part due to the highly addictive nature of nicotine and the strong nicotine withdrawal symptoms that can occur when one begins to deprive the body of the nicotine. Overcoming nicotine withdrawal symptoms is a critical challenge for those attempting to conquer nicotine dependence.

A wide variety of nicotine cessation products and therapies are known. However, in most of the cases the mere replacement of cigarettes with another nicotine source may not be sufficient to ensure success in smoking cessation therapy. The available nicotine cessation products include lozenges, gums, transdermal patches and the like. Lozenges and chewing gums provide oral delivery of nicotine, whereas transdermal patch treatments deliver nicotine through the wearer's skin.

Nicotine chewing gum containing nicotine polacrilex and transdermal nicotine are two of the more popular forms of nicotine replacement available commercially.

Nicotine gum is actually an ion-exchange resin that releases nicotine slowly when the patient chews and the nicotine present in the mouth is delivered directly to the systemic circulation by buccal absorption. However, much of the nicotine is retained in the gum through incomplete chewing or is largely wasted through swallowing, so that the systemic bioavailability of nicotine from gum is low and averages only 30-40%.

Furthermore, most commercially available products such as chewing gums, lozenges for nicotine replacement in smoking cessation therapy do not specifically address the issue of taste masking and side effects of nicotine ingestion such as nausea and burning sensation. Instead, they generally target providing a stable baseline level of nicotine in the blood.

The following patents/patent applications disclose compositions containing nicotine.

U.S. Pat. No. 4,967,773 discloses a lozenge formed by compression of at least two mixed components, one of said components including lactose or a lactose containing substance and the other of said components comprising a carrier having nicotine or a nicotine derivative absorbed therein such that there is no direct contact between the nicotine and the lactose whilst together in the lozenge.

GB2230439 discloses a lozenge which is a substitute for smoking tobacco comprises a lozenge core which contains nicotine and/or a nicotine substitute and a shell or coating around the lozenge core.

GB2299756 discloses pastilles containing nicotine in an acacia gum or gelatine base.

U.S. Pat. No. 5,488,962 discloses chewing gum formed into 3 g strips, characterized in that each strip contains not more than 25 wt. % of a gum base and from 0.3-0.4 mg of nicotine dispersed in the gum base.

U.S. Pat. No. 6,183,775 discloses a controlled release lozenge consisting of (a) 50 to 99% of a soluble filler; (b) 0.5 to 30% of an insoluble film forming agent which is selected from the group consisting of a polyacrylate, ethyl cellulose and mixtures thereof; (c) 0.5 to 30% of a swellable polymer which is selected from the group consisting of xanthan gum, guar gum, cellulose derivatives and mixtures thereof; and (d) nicotine or a salt or derivative of nicotine.

U.S. Pat. No. 6,280,761 discloses a nicotine lozenge consisting of nicotine, mannitol, xylitol, mint flavor, ammonium glycyrrhizinate, sodium carbonate, sodium bicarbonate, hydrogenated vegetable oil and magnesium stearate.

U.S. Pat. No. 6,344,222 discloses a chewing gum composition for systemic, oral administration of nicotine constituent, said composition comprising a) a nicotine constituent; b) a gum base matrix, said gum base matrix including at least one hydrophilic polymer and at least one hydrophobic polymer; and c) a buffer.

US2004151771 discloses a flavored a lozenge comprising a sustained release wet matrix of ethylcellulose and a flavoring agent selected from essential oils, constituents of essential oils, and mixtures thereof, wherein, in an aqueous environment, the matrix gradually releases the flavoring agent over a time period of at least 45 minutes. The active ingredient used is nicotine US2005034738 discloses a chewing tobacco substitute comprising a non-tobacco leaf-like material; an alkaline chemical; and a nicotine compound capable of being absorbed orally. The nicotine compound used is nicotine polacrilex.

US2005002993 discloses a confectionery product for delivering at least one pharmaceutically active agent [such as nicotine replacement agents] which includes a hard outer shell and a core comprised of a core material which is or forms a liquid-like to a gel-like substance in the oral cavity and is capable of delivering pharmaceutically active agents to infected and/or irritated tissues of the throat.

US2005123502 discloses an oral composition comprising a nicotine active, a polycarbophil component or a salt thereof and an alginic acid component or a salt thereof.

US20050053665 discloses a nicotine-containing pharmaceutical composition comprising nicotine and cellulose of non-seed organism origin. Said composition can be in the form of chewing gum, mouth spray, buccal sachet, lozenge or a tablet.

US2007269492 discloses a coated oral dosage forms for the delivery of nicotine in any form to a subject by rapid intraoral delivery of nicotine comprising at least one core, nicotine in any form and/or a nicotine mimicking agent, at least one coating layer and optionally at least one additive.

US2007269386 discloses a buffered pharmaceutical oral formulation comprising nicotine, characterized in that it is buffered with at least trometamol. The formulation can be in the form of a mouth spray, a capsule, a chewing gum, a chewable tablet, a tablet, a melt tablet and a lozenge.

International Publication No. WO/2009/134947 discloses an oral lozenge composition comprising: a) a master granule component comprising: at least one an alkaline buffering agent; at least one dissolution modifier; and at least one filler; b) a nicotine polacrilex; and c) at least one alkaline buffering agent. The dissolution modifier used is selected from the group consisting of xanthan gum, acacia, carbomer, carboxymethylcellulose, carrageenan and cellulose.

US20100004294 discloses a lozenge composition for achievement of a fast onset of action of nicotine after application of the solid dosage form to the oral cavity of a subject, comprising a nicotine-cellulose combination and one or more pharmaceutically acceptable excipients.

Short comings and problems associated with the known nicotine containing compositions:

Nicotine containing products in the form of chewing gums are associated with problems such as disposal problem and chewing is very often socially unacceptable.

Further, much of the nicotine is retained in the gum through incomplete chewing or is largely wasted through swallowing which in turn results in low systemic bioavailability (about 30 to 40%).

Furthermore, chewing of chewing gum leads to breaking of polymer coating and result in excessive release of nicotine in buccal cavity which in turn causes nausea, bad taste and burning sensation.

Nicotine containing lozenges also possess disadvantages such as person using such lozenges is not comfortable to keep a hard product in the buccal cavity for prolong period. Another disadvantage is that lozenges get break down into pieces followed by accidental swallowing which in turn result in excessive transfer of nicotine in GI tract and causes nausea and burning sensation.

Accordingly, it is desirable to develop a palatable nicotine containing formulation which is devoid of gums and which releases the nicotine for prolong period of time in controlled manner without causing nausea, bad taste and burning sensation.

SUMMARY OF THE INVENTION

It is an object of the present invention to provide a formulation which can be used by smokers either as a substitute for cigarettes or the like or as an aid in giving up the smoking habit or for nicotine replacement in smoking cessation therapy.

It is another object of the present invention to provide a formulation which is designed to be held in the user's mouth and sucked to release active ingredient into the buccal cavity in a user determined manner.

It is still another object of the present invention to provide a formulation which provides maximum buccal absorption of nicotine.

It is yet another object of the present invention to provide a formulation which is not associated with symptoms like nausea, hiccups or burning sensation.

It is a further object of the present invention to provide an oral formulation which releases the active ingredient for prolong period of time in a controlled manner.

In accordance with the present invention there is provided a soft pastille comprising:

a. nicotine active in an amount of about 0.05% to about 1% of the mass of the pastille;
b. gelling agent in an amount of about 5% to about 40% of the mass of the pastille;
c. plasticizer in an amount of about 30% to about 70% of the mass of the pastille;
d. sweetener in an amount of about 0.05% to about 10% of the mass of the pastille;
e. releasing agent in an amount of about 0.5% to about 30% of the mass of the pastille;
f. preservative in an amount of about 0.05% to about 2% of the mass of the pastille;
g. flavouring agent in an amount of about 0.01% to 5% of the mass of the pastille; and
h. water in an amount of about 5% to about 20% of the mass of the pastille, said pastille being capable of being dissolved in the buccal cavity in about 5 to about 15 minutes, depending on the user's sucking pattern.

Typically, the nicotine active is selected from the group consisting of nicotine polacrilex, tobacco plant extract containing nicotine, derivatives of nicotine, nicotine oil, nicotine salts, nicotine cation exchanger, nicotine inclusion complex, nicotine bound to cellulose or starch micro-spheres, metabolites of nicotine and combinations thereof.

Preferably, the nicotine active is nicotine polacrilex or tobacco plant extract containing nicotine.

Typically, the gelling agent is selected from the group consisting of gelatin, carrageenan and mixtures thereof.

Preferably, the gelling agent is gelatin.

Typically, the ratio of the gelling agent to plasticizer is in the range of about 1:2.7 to about 1:3.

Typically, the plasticizer is selected from the group consisting of glycerine, sorbitol and mixtures thereof.

Preferably, the plasticizer is glycerine

Typically, the releasing agent is selected from the group consisting of lecithin, oil, starch and mixtures thereof.

Preferably, the releasing agent is lecithin.

Typically, the sweetener is at least one selected from the group consisting of stevia, aspartame, saccharin, sucralose, sucrose, dextrose and lactose.

Typically, the preservative is at least one selected from the group consisting of methyl paraben, propyl paraben, sodium methyl paraben and sodium propyl paraben.

Typically, the flavouring agents include, but are not limited to menthol, vanillin, peppermint, lemon, mint, strawberry, banana, pineapple, orange, raspberry and the like.

In accordance with another aspect of the present invention there is also provided a process for the preparation of soft pastilles; said process comprising the following steps:
 a. introducing accurately weighed plasticizer selected from the group consisting of glycerine, sorbitol and combinations thereof and water in a reactor followed by addition of gelling agent selected from the group consisting of gelatin, carrageenan and mixtures thereof and releasing agent selected from the group consisting of lecithin, oil, starch and combinations thereof to form a first mixture;
 b. adding Nicotine active selected from the group consisting of nicotine polacrilex, tobacco plant extract containing nicotine, derivatives of nicotine, nicotine oil, nicotine salts, nicotine cation exchanger, nicotine inclusion complex, nicotine bound to cellulose or starch microspheres, metabolites of nicotine and combinations thereof to the mixture and mixing for about 30 to about 45 minutes at 1500 rpm to form a second mixture;
 c. incorporating adequate quantities of sweetener, flavouring agent, colour and preservative into the second mixture to obtain a mass;
 d. collecting the mass in a container followed by cooling and solidification;
 e. transferring the solidified mass into a melter to obtain a melted mass; and
 f. passing the melted mass through an injector into the preformed cavities followed by cooling and blister packaging.

DETAILED DESCRIPTION OF THE INVENTION

In accordance with the present invention there is provided a soft pastille comprising:
 a. nicotine active in an amount of about 0.05% to about 1% of the mass of the pastille;
 b. gelling agent in an amount of about 5% to about 40% of the mass of the pastille;
 c. plasticizer in an amount of about 30% to about 70% of the mass of the pastille;
 d. sweetener in an amount of about 0.05% to about 10% of the mass of the pastille;
 e. releasing agent in an amount of about 0.5% to about 30% of the mass of the pastille;
 f. preservative in an amount of about 0.05% to about 2% of the mass of the pastille;
 g. flavouring agent in an amount of about 0.01% to 5% of the mass of the pastille; and
 h. water in an amount of about 5% to about 20% of the mass of the pastille,
said pastille is capable of being dissolved in the buccal cavity in about 5 to about 15 minutes, depending on the user's sucking pattern.

Typically, the nicotine active is selected from the group consisting of nicotine polacrilex, tobacco plant extract containing nicotine, derivatives of nicotine, nicotine oil, nicotine salts, nicotine cation exchanger, nicotine inclusion complex, nicotine bound to cellulose or starch micro-spheres, metabolites of nicotine and combinations thereof.

In accordance with one of the preferred embodiment of the present invention the nicotine active is nicotine polacrilex.

In accordance with another preferred embodiment of the present invention the nicotine active is tobacco plant extract containing nicotine.

The gelling agent used for the preparation of soft pastille in accordance with the present invention is selected from the group consisting of gelatin, carrageenan and mixtures thereof.

In accordance with the preferred embodiment of the present invention gelatin is used as a gelling agent as the gel obtained from gelatin is thermo-reversible. Because of thermo-reversible property, after cooling the gelatin solution the viscosity increases progressively and passes from a sol to a gel. On the other hand, if the gel is heated, it dissolves and once again becomes a solution.

Typically, the plasticizer is selected from the group consisting of glycerine, sorbitol and mixtures thereof.

In accordance with the preferred embodiment of the present invention the plasticizer used is glycerine.

The critical parameter in the preparation of soft pastille in accordance with the present invention is the ratio of the gelling agent to plasticizer. It is found that when the ratio of gelling agent to glycerin is kept below 1:2.7, the formed mixture becomes hard and gets stuck in the nozzle while transferring it into the die cavities in order to form pastilles. It is also found that when the ratio of gelling agent to glycerin is kept above 1:3, the formed mixture becomes less viscous and results in formation of poor quality pastilles.

Therefore, the ratio of gelling agent to glycerin for the preparation of soft pastilles containing nicotine is kept in the range of about 1:2.7 to about 1:3.

Typically, the releasing agent is selected from the group consisting of lecithin, oil, starch and mixtures thereof.

In accordance with the preferred embodiment of the present invention the releasing agent used in the preparation of soft pastilles containing nicotine is lecithin. Lecithin used in the preparation of soft pastilles acts as a releasing agent or lubricating agent which prevent the friction (or sticking) between the die wall and the pastilles. This in turn helps to eject or remove the pastilles smoothly from the die cavity as well as from the final pack.

The sweetener used in the preparation of pastilles in accordance with the present invention is at least one selected from the group consisting of stevia, aspartame, saccharin, sucralose, sucrose, dextrose and lactose.

Typically, the preservative is at least one selected from the group consisting of methyl paraben, propyl paraben, sodium methyl paraben and sodium propyl paraben.

The flavouring agents employed in the preparation of pastilles of the present invention include, but are not limited to menthol, vanillin, peppermint, lemon, mint, strawberry, banana, pineapple, orange, raspberry and the like.

In accordance with another aspect of the present invention there is also provided a process for the preparation of soft pastilles; said process comprising the following steps:

First step is introducing accurately weighed plasticizer selected from the group consisting of glycerine, sorbitol and combinations thereof and water in a reactor. To this accurately weighed gelling agent selected from the group consisting of gelatin, carrageenan and mixtures thereof and releasing agent selected from the group consisting of lecithin, oil, starch and combinations thereof are added to form a first mixture.

To this first mixture, Nicotine active selected from the group consisting of nicotine polacrilex, tobacco plant extract containing nicotine, derivatives of nicotine, nicotine oil, nicotine salts, nicotine cation exchanger, nicotine inclusion complex, nicotine bound to cellulose or starch micro-spheres, metabolites of nicotine and combinations thereof is added and the resulted mixture is mixed for about 30 to about 45 minutes at 1500 rpm to form a second mixture.

In next step, adequate quantities of sweetener, flavour, colour and preservative are incorporated into the second mixture to obtain a mass. The obtained mass is then collected in a container followed by cooling and solidification of the mass. The solidified mass is transferred into a melter to obtain a melted mass.

Finally, the melted mass is passed through an injector into the preformed cavities followed by cooling and blister packaging.

Following examples illustrate the invention, but is not intended to limit the scope of the present invention.

Example 1

A soft pastille in accordance with the present invention was prepared with the following composition.

| Each pastille (1500 mg) contains: | |
| --- | --- |
| Nicotine from Nicotine poliacrilex (1 mg = 5 mg): | 5 mg |
| Gelatin (bloom strength 250): | 299 mg |
| Glycerine: | 971.7 mg |
| Water: | 170 mg |
| Lecithin: | 37.3 mg |
| Flavour: | 3.8 mg |
| Sucralose: | 1.4 mg |
| Colour: | 4 mg |
| Methyl paraben: | 2.4 mg |
| Propyl paraben: | 1.2 mg |

Example 2

| Each pastille (1500 mg) contains: | |
| --- | --- |
| Nicotine from Nicotine poliacrilex (1 mg = 5 mg): | 5 mg |
| Gelatin(bloom strength 170): | 315 mg |
| Glycerine: | 950 mg |
| Water: | 188 mg |
| Lecithin: | 30.3 mg |
| Flavour: | 2.8 mg |
| Sucralose: | 2 mg |
| Colour: | 4 mg |
| Methyl paraben: | 2.4 mg |
| Propyl paraben: | 1.2 mg |

Example 3

| Each pastille (1500 mg) contains: | |
| --- | --- |
| Nicotine from Nicotine poliacrilex (1 mg = 5 mg): | 5 mg |
| Gelatin (bloom strength 100): | 343 mg |
| Glycerine: | 970 mg |
| Water: | 150 mg |
| Lecithin: | 25.6 mg |
| Methyl paraben: | 2.4 mg |
| Propyl paraben: | 1.2 mg |
| Spearmint: | 1.5 mg |
| Menthol: | 1.3 mg |
| Sucralose: | 1.5 mg |
| Colour: | 4 mg |

[Nicotine Polacrilex contain 20% Nicotine; 1 mg of Nicotine Polacrilex=0.2 mg of Nicotine]

Testing:

A] Stability Data:

I] Temperature: 25° C.±2° C.; Relative Humidity: 60±5%

TABLE NO. 1

| Time interval [Month] | Average Weight (±7.5%) (in mg) | Uniformity of Weight (±7.5%) | Assay/uniformity of content [90% to 115% of Label Claim] |
| --- | --- | --- | --- |
| 0 | 1509.22 | Complies | 110.43% |
| 3 | 1500.87 | Complies | 108.72% |
| 6 | 1503.42 | Complies | 106.98% |
| 9 | 1500.51 | Complies | 104.23% |
| 12 | 1501.92 | Complies | 102.49% |
| 18 | 1502.51 | Complies | 101.31% |
| 24 | 1506.92 | Complies | 99.56% |

II] Temperature: 30° C.±2° C.; Relative Humidity: 65±5%

TABLE NO. 2

| Time interval [Month] | Average Weight (±7.5%) (in mg) | Uniformity of Weight (±7.5%) | Assay/uniformity of content [90% to 115% of Label Claim] |
| --- | --- | --- | --- |
| 0 | 1509.22 | Complies | 110.43% |
| 3 | 1509.55 | Complies | 107.67% |
| 6 | 1501.97 | Complies | 105.12% |
| 9 | 1509.60 | Complies | 103.89% |
| 12 | 1506.87 | Complies | 100.32% |

III] Temperature: 40° C.±2° C.; Relative Humidity: 75±5%

TABLE NO. 3

| Time interval [Month] | Average Weight (±7.5%) (in mg) | Uniformity of Weight (±7.5%) | Assay/uniformity of content [90% to 115% of Label Claim] |
| --- | --- | --- | --- |
| 0 | 1509.22 | Complies | 110.43% |
| 3 | 1508.34 | Complies | 106.21% |
| 6 | 1505.43 | Complies | 103.68% |

From the above stability data it is found that the product of this invention is stable.

B] Dissolution Study [User Defined]:

Each of the 10 subjects was instructed to hold and suck the pastille of the present invention. The time required to completely dissolve the pastille in the mouth was recorded by each of the subjects.

The results are provided in Table No. 4

TABLE NO. 4

| Subject | Dissolution time [min.] |
| --- | --- |
| 1 | 8 |
| 2 | 12 |
| 3 | 10 |
| 4 | 5 |
| 5 | 10 |
| 6 | 9 |
| 7 | 15 |
| 8 | 9 |
| 9 | 10 |
| 10 | 13 |

From the results (as shown in Table No. 4) it was found that the time require to dissolve the pastille of the present invention is in between 5 to 15 minutes depending upon individual's rate of sucking the pastille. The average dissolution time was found to be 10 Minutes.

C] Determination of Nicotine Craving:

As nicotine craving is considered to be the most consistent and most severe factor in preventing a person from quitting smoking. Ultimately, the smoker's active involvement with timely self-assessment of the craving is very crucial for the efficacy of a smoking cessation program.

Nicotine craving depends upon daily stress patterns, sleep and eating habits, body weight, previous smoking levels and the like. Thus, the desire or need for pastilles (comparable to the desire to smoke cigarettes) typically will vary during any given day and from day to day, as well as from patient to patient.

A variety of methods have been reported to assess the craving for nicotine, which include but are not limited to, the nicotine craving test specified by the Diagnostic and Statistical Manual of Mental Disorders, Revised Third Edition (DSM-III-R) (see (1991) J. Am. Med. Assoc. 266:3133); the Shiffman-Jarvik Craving Subscale (see O'Connell and Martin (1987) J. Consult. Clin. Psychol. 55:367-371 and Steur and Wewers (1989) ONF 16:193-198, also describing a parallel visual analog test); West et al. (1984) Br. J. Addiction 79:215-219; and Hughes et al. (1984) Psychopharmacology 83:82-87, each of which is expressly incorporated herein by reference.

As described in the J. Am. Med. Assoc. 266:3133, at page 3135, nicotine withdrawal symptoms, specified by the DSM-III-R, are scored based on the following symptoms: nicotine craving, irritability, frustration, anger, anxiety, difficulty concentrating, and restlessness. Severity of each symptom is rated as (0) none, (1) slight, (2) mild, (3) moderate, or (4) severe. A mean combined withdrawal symptom score is calculated for each patient as the average of the individual symptom scores.

In the context of the present invention, nicotine craving scale as taught in DSM-III-R, has been employed for assessment of craving of the subjects.

According to this scale, a subject is asked to rate his craving for nicotine, as well as his level of irritability, frustration, anger, anxiety, difficulty in concentrating and restlessness. Severity of each symptom is then rated on a scale between 0 and 4, wherein 0 is none; 1 is slight; 2 is mild; 3 is moderate; and 4 is severe. The mean combined withdrawal symptom score is calculated for the subject as the average of all of the symptom scores.

C] I: A randomized double blind, placebo controlled trial of nicotine soft gelatin pastille prepared in accordance with the present invention was carried out in 20 subjects who were addicted to cigarette smoking.

Group A: 10 subjects who received nicotine soft gelatin pastille [Pastille containing 2 mg of nicotine] and Group B: 10 subjects who received placebo.

TABLE 5

Results of withdrawal symptoms in participants of group A

| Withdrawal symptoms | 1 (Age: 42, Sex: M) | 2 (Age: 61, Sex: M) | 3 (Age: 37, Sex: M) | 4 (Age: 26, Sex: M) | 5 (Age: 31, Sex: M) | 6 (Age: 48, Sex: M) | 7 (Age: 29, Sex: F) | 8 (Age: 23, Sex: F) | 9 (Age: 43, Sex: M) | 10 (Age: 52, Sex: M) |
|---|---|---|---|---|---|---|---|---|---|---|
| Craving | 2 | 2 | 0 | 1 | 3 | 2 | 1 | 2 | 1 | 1 |
| Irritability | 0 | 1 | 2 | 1 | 2 | 1 | 2 | 3 | 2 | 2 |
| Frustration | 3 | 2 | 2 | 0 | 1 | 2 | 2 | 4 | 2 | 1 |
| Anger | 0 | 3 | 1 | 3 | 1 | 2 | 1 | 1 | 2 | 2 |
| Anxiety | 1 | 0 | 1 | 2 | 1 | 3 | 0 | 1 | 0 | 2 |
| Difficulty in concentrating | 1 | 1 | 0 | 1 | 2 | 0 | 2 | 0 | 1 | 1 |
| Restlessness | 4 | 1 | 3 | 2 | 1 | 2 | 3 | 2 | 3 | 3 |
| Average | 1.57 | 1.43 | 1.29 | 1.43 | 1.57 | 1.71 | 1.57 | 1.86 | 1.57 | 1.71 |

Group withdrawal symptom score: 1.57
(Arithmetic mean of the averages of the individual withdrawal symptoms)

TABLE 6

Results of withdrawal symptoms in participants of group B

| Withdrawal symptoms | 1 (Age: 25, Sex: M) | 2 (Age: 39, Sex: F) | 3 (Age: 57, Sex: M) | 4 (Age: 24, Sex: M) | 5 (Age: 64, Sex: M) | 6 (Age: 28, Sex: M) | 7 (Age: 34, Sex: F) | 8 (Age: 42, Sex: M) | 9 (Age: 36, Sex: M) | 10 (Age: 29, Sex: M) |
|---|---|---|---|---|---|---|---|---|---|---|
| Craving | 4 | 3 | 4 | 4 | 3 | 4 | 4 | 3 | 3 | 4 |
| Irritability | 4 | 4 | 3 | 4 | 4 | 4 | 3 | 4 | 3 | 4 |
| Frustration | 3 | 4 | 3 | 4 | 3 | 4 | 2 | 4 | 4 | 3 |
| Anger | 4 | 3 | 4 | 4 | 4 | 3 | 4 | 3 | 2 | 4 |
| Anxiety | 3 | 2 | 4 | 3 | 4 | 4 | 3 | 4 | 4 | 3 |
| Difficulty in concentrating | 2 | 4 | 3 | 4 | 4 | 3 | 4 | 4 | 4 | 4 |
| Restlessness | 4 | 3 | 4 | 4 | 3 | 4 | 4 | 3 | 4 | 3 |
| Average | 3.43 | 3.29 | 3.57 | 3.86 | 3.57 | 3.71 | 3.43 | 3.57 | 3.43 | 3.57 |

Group withdrawal symptom score: 3.54
(Arithmetic mean of the averages of the individual withdrawal symptoms)

From the observations as shown in the table No. 5 & 6 it was found that the placebo group reported significantly more severe withdrawal symptoms than the nicotine subjects.

C] II: Another randomized double blind, placebo controlled trial of nicotine soft gelatin pastille prepared in accordance with the present invention was carried out in 20 subjects who were addicted to tobacco chewing.
Group A: 10 subjects who received nicotine soft gelatin pastille [Pastille containing 4 mg of nicotine]
Group B: 10 subjects who received placebo Group withdrawal symptom score: 3.58
(Arithmetic mean of the averages of the individual withdrawal symptoms)

From the observations as shown in the table No. 7 & 8 it was found that the placebo group reported significantly more severe withdrawal symptoms than the nicotine subjects.

D] Overall Compliance and Tolerance Study:
D] I: An independent study was undertaken to compare the effect of the existing nicotine lozenges and the pastilles of the present invention on specific parameters related to the overall compliance and tolerance.

The study was carried out on 10 subjects (addicted to cigarette smoking) who were divided in to groups of 5 each.

TABLE 7

Results of withdrawal symptoms in participants of group A

| Withdrawal symptoms | 1 (Age: 57, Sex: M) | 2 (Age: 29, Sex: M) | 3 (Age: 31, Sex: M) | 4 (Age: 22, Sex: M) | 5 (Age: 41, Sex: M) | 6 (Age: 62, Sex: M) | 7 (Age: 45, Sex: M) | 8 (Age: 47, Sex: M) | 9 (Age: 36, Sex: M) | 10 (Age: 54, Sex: M) |
|---|---|---|---|---|---|---|---|---|---|---|
| Craving | 2 | 0 | 1 | 1 | 0 | 3 | 1 | 2 | 0 | 1 |
| Irritability | 1 | 2 | 1 | 0 | 3 | 1 | 2 | 0 | 2 | 3 |
| Frustration | 1 | 3 | 2 | 3 | 1 | 2 | 3 | 1 | 1 | 2 |
| Anger | 3 | 1 | 2 | 2 | 1 | 1 | 1 | 2 | 3 | 2 |
| Anxiety | 1 | 2 | 1 | 2 | 1 | 0 | 1 | 1 | 1 | 1 |
| Difficulty in concentrating | 2 | 1 | 2 | 1 | 3 | 2 | 3 | 2 | 2 | 2 |
| Restlessness | 1 | 3 | 2 | 3 | 2 | 2 | 1 | 2 | 2 | 1 |
| Average | 1.57 | 1.71 | 1.57 | 1.71 | 1.57 | 1.57 | 1.71 | 1.42 | 1.57 | 1.71 |

Group withdrawal symptom score: 1.61
(Arithmetic mean of the averages of the individual withdrawal symptoms)

Group I: 5 subjects were administered the pastilles [pastille containing 2 mg of nicotine] of the present invention while subjects of Group II were administered nicotine lozenges.

TABLE 8

Results of withdrawal symptoms in participants of group B

| Withdrawal symptoms | 1 (Age: 46, Sex: M) | 2 (Age: 33, Sex:: M) | 3 (Age: 28, Sex: M) | 4 (Age: 37, Sex: M) | 5 (Age: 42, Sex: M) | 6 (Age: 54, Sex: M) | 7 (Age: 50, Sex: M) | 8 (Age: 38, Sex: M) | 9 (Age: 56, Sex: M) | 10 (Age: 32, Sex:: M) |
|---|---|---|---|---|---|---|---|---|---|---|
| Craving | 4 | 4 | 3 | 4 | 4 | 4 | 4 | 3 | 4 | 4 |
| Irritability | 3 | 2 | 4 | 4 | 3 | 3 | 3 | 4 | 4 | 4 |
| Frustration | 4 | 4 | 4 | 4 | 4 | 2 | 4 | 4 | 3 | 3 |
| Anger | 4 | 3 | 3 | 2 | 4 | 4 | 4 | 4 | 2 | 4 |
| Anxiety | 2 | 4 | 4 | 4 | 3 | 4 | 2 | 4 | 4 | 3 |
| Difficulty in concentrating | 4 | 4 | 4 | 3 | 3 | 4 | 4 | 3 | 4 | 4 |
| Restlessness | 4 | 3 | 4 | 4 | 4 | 3 | 4 | 4 | 4 | 4 |
| Average | 3.57 | 3.43 | 3.71 | 3.57 | 3.57 | 3.43 | 3.57 | 3.71 | 3.57 | 3.71 |

The observations are provided in Table 9 & 10 given below:

TABLE 9

| | Group I | | | | |
|---|---|---|---|---|---|
| | | Subjects | | | |
| Parameter | Subject 1 | Subject 2 | Subject 3 | Subject 4 | Subject 5 |
| Nausea | − | − | − | − | − |
| Headache | − | − | − | − | − |
| Hiccups | + | − | − | − | − |
| Burning sensation | − | − | − | − | − |
| Palatability | +++++ | +++ | ++++ | ++++ | ++++ |

[On a scale of 1 to 5, +: presence & −: absence]

TABLE 10

| | Group II | | | | |
|---|---|---|---|---|---|
| | | Subjects | | | |
| Parameter | Subject 1 | Subject 2 | Subject 3 | Subject 4 | Subject 5 |
| Nausea | ++ | ++ | +++ | ++++ | + |
| Headache | + | ++ | + | + | + |
| Hiccups | − | + | ++ | − | ++ |
| Burning sensation | + | ++ | + | +++ | + |
| Palatability | −−− | −− | + | −−− | −−−− |

In case of Group I, from the observations as provided in Table 9, it was found that all the subjects reported better mouth-feel effect (palatability), the reason being, the pastilles of the present invention unlike the lozenges were soft and flexible without any hard edges. Furthermore, the pastilles were elastic in nature and did not cause any local irritation in the oral mucosa. Still furthermore, none of the subjects reported nausea, headache and burning sensation which are very often observed in case of nicotine lozenges on account of abrupt rupture in the mouth cavity, which in turn suddenly caused sharp increase in the Nicotine levels. As regards to the other parameters like hiccups, only one patient reported minor hiccup.

As regards to Group II, all of the subjects except one reported discomfort with hardness and edges of the lozenges. Furthermore, each of the subjects also reported burning sensation. Severe to moderate headache and nausea was reported by all the subjects. Furthermore, hiccups with moderate severity were also reported in 3 of the subjects.

D] II: Another independent study was undertaken to compare the effect of the existing nicotine lozenges and the pastilles of the present invention on specific parameters related to the overall compliance and tolerance.

The study was carried out on 10 subjects (addicted to tobacco chewing) who were divided in to groups of 5 each.
Group I: 5 subjects were administered the pastilles [pastille containing 4 mg of nicotine] of the present invention while Group II were administered nicotine lozenges.

The observations are provided in Table 11 & 12 given below:

TABLE 11

| | Group I | | | | |
|---|---|---|---|---|---|
| | | Subjects | | | |
| Parameter | Subject 1 | Subject 2 | Subject 3 | Subject 4 | Subject 5 |
| Nausea | − | − | + | − | + |
| Headache | − | − | − | − | − |
| Hiccups | − | − | + | − | − |
| Burning sensation | − | − | − | − | − |
| Palatability | +++ | ++++ | +++ | +++++ | ++++ |

[On a scale of 1 to 5, +: presence & −: absence]

TABLE 12

| | Group II | | | | |
|---|---|---|---|---|---|
| | | Subjects | | | |
| Parameter | Subject 1 | Subject 2 | Subject 3 | Subject 4 | Subject 5 |
| Nausea | ++++ | +++ | +++ | ++ | ++ |
| Headache | ++ | + | ++ | + | + |
| Hiccups | + | + | ++ | + | ++ |
| Burning sensation | ++ | +++ | ++ | +++ | + |
| Palatability | −−− | −− | − | −−− | −−−− |

In case of Group I, from the observations as provided in Table 11, it was found that out of 5 two subjects reported minor nausea. Further, all the subjects reported better mouth-feel effect (palatability). Still furthermore, none of the subjects reported headache and burning sensation while only one participant reported minor hiccup.

As regards to Group II, all of the subjects reported discomfort with hardness and edges of the lozenges. Furthermore, each of the subjects also reported moderate to severe nausea, burning sensation and hiccups.

It was found out that the pastilles of the present invention offered improved tolerance (in terms of symptoms) and compatibility as compared to the known lozenges from the market. Thus the product of the present invention provides better patient compliance.

E] Smoking Cessation Study:

A study was carried out in 20 subjects addicted to cigarette smoking and/or tobacco chewing. After initial interviews for collection of the patient details, based on the average number cigarettes smoked by each of the subjects, the dose and frequency of the pastille administration was decided. Accordingly, the following table shows the groups in which all the subjects were divided into along with the respective dose and frequency of the pastilles administered to each of the groups.

For subjects who had a history of obsessive tobacco chewing, pastilles with high nicotine content were given.

TABLE 13

| | Group description | Dose | Frequency |
|---|---|---|---|
| Group 1 | Subjects who smoke on average 10 cigarettes/day | 1 mg | 10 per day |
| Group 2 | Subjects who smoke on average 20 cigarettes/day | 2 mg | 10 per day |
| Group 3 | Subjects who smoke more than 20 cigarettes/day on average. | 4 mg | 10 per day |
| Group 4 | Subjects with tobacco chewing addiction | 4 mg | 10 per day |

Almost all the subjects had a history of more than 2 years of cigarette/tobacco chewing addiction. In view of this, the subjects were observed for a period of 3 months.

During the study period, there were 2 phases. In the first phase, the subjects were encouraged to substitute smoking/tobacco chewing by pastille consumption; in the second phase (i.e. once the subject has switched to pastille consumption without the need for smoking) the subjects were encouraged to taper down the frequency of pastille consumption for attaining the ultimate goal of successful quitting. The duration of the first phase and the second phase was varied from subject to subject depending on the response shown by the subject.

A subject is said to have successfully quit smoking in this context when he/she no longer smokes or consumes nicotine through any other means which also include the pastilles of the present invention.

Group 1:

All the subjects completed the study. All of the subjects successfully quit smoking after participation for a period of 1 week to 3 weeks of the study period. As the study progressed, the initial dosing frequency was gradually tapered in consonance with the craving of each of the subjects.

Group 2:

One of the subjects abruptly discontinued the study on 4$^{th}$ day from the commencement of the study. Right from the first week of the study period, the subjects were constantly encouraged to substitute smoking by pastille consumption. (First Phase).

Out of the remaining 4 subjects, 3 successfully quit smoking after participating for a period of 3 to 5 weeks while the remaining one continued consuming pastilles without smoking (Phase 2) till the final week of the study period. However, the frequency of the pastille consumption at the end of the study period was only 2 pastilles per day.

Group 3:

One of the five subjects successfully quit smoking at the end of 4$^{th}$ week of the study period. Another one quit smoking altogether; however he continued the consumption of pastilles at a frequency of 2 pastilles per day till the end of the study period (Phase2). Still another subject also quit smoking during the study period but his pastilles consumption frequency was 8 per day as reported on the last day of the study period. Out the of remaining 2 subjects, one subject reported that his smoking frequency during the study period came down to 6 a day but he still continued with pastille consumption with a frequency of 2 pastille per day (Phase 1).

Group 4:

One of the total five subjects successfully quit smoking at the end of eight weeks of the study period.

During Phase 1, out of the 5 subjects, 2 could completely switch to the Phase 2 (Pastille only). The frequency of 2 of the subjects who switched to Phase 2 was 10 pastilles (2 mg) per day as reported on the last day of the study period.

The two subjects who could not switch to phase 2 of the study reported reduction in frequency of tobacco chewing to just 2 times a day along with pastille consumption frequency of 2 pastilles (2 mg) per day.

While considerable emphasis has been placed herein on the specific ingredients of the preferred formulation, it will be appreciated that many additional ingredients can be added and that many changes can be made in the preferred formulation without departing from the principles of the invention. These and other changes in the preferred formulation of the invention will be apparent to those skilled in the art from the disclosure herein, whereby it is to be distinctly understood that the foregoing descriptive matter is to be interpreted merely as illustrative of the invention and not as a limitation.

The invention claimed is:

1. A soft pastille comprising:
   a. nicotine active in an amount of about 0.05% to about 1% of the mass of the pastille;
   b. gelling agent in an amount of about 5% to about 40% of the mass of the pastille;
   c. plasticizer in an amount of about 30% to about 70% of the mass of the pastille;
   d. sweetener in an amount of about 0.05% to about 10% of the mass of the pastille;
   e. releasing agent in an amount of about 0.5% to about 30% of the mass of the pastille;
   f. preservative in an amount of about 0.05% to about 2% of the mass of the pastille;
   g. flavouring agent in an amount of about 0.01% to 5% of the mass of the pastille; and
   h. water in an amount of about 5% to about 20% of the mass of the pastille, said pastille being capable of being dissolved in the buccal cavity in about 5 to about 15 minutes, depending on the user's sucking pattern; and
   a ratio of the gelling agent to the plasticizer being in a range of about 1:2.7 to about 1:3.

2. The pastille as claimed in claim 1, wherein the nicotine active is selected from the group consisting of nicotine polacrilex, tobacco plant extract containing nicotine, nicotine oil, nicotine salts, nicotine cation exchanger, nicotine inclusion complex, nicotine bound to cellulose or starch micro-spheres, and combinations thereof.

3. The pastille as claimed in claim 1, wherein the nicotine active is nicotine polacrilex or tobacco plant extract containing nicotine.

4. The pastille as claimed in claim 1, wherein the gelling agent is selected from the group consisting of gelatin, carrageenan and mixtures thereof.

5. The pastille as claimed in claim 1, wherein the gelling agent is gelatin.

6. The pastille as claimed in claim 1, wherein the plasticizer is selected from the group consisting of glycerine, sorbitol and mixtures thereof.

7. The pastille as claimed in claim 1, wherein the plasticizer is glycerine.

8. The pastille as claimed in claim 1, wherein the releasing agent is at least one selected from the group consisting of lecithin, oil and starch.

9. The pastille as claimed in claim 1, wherein the releasing agent is lecithin.

10. The pastille as claimed in claim 1, wherein the sweetener is at least one selected from the group consisting of stevia, aspartame, saccharin, sucralose, sucrose, dextrose and lactose.

11. The pastille as claimed in claim 1, wherein the preservative is at least one selected from the group consisting of methyl paraben, propyl paraben, sodium methyl paraben and sodium propyl paraben.

12. The pastille as claimed in claim 1, wherein the flavouring agent is at least one selected from the group consisting of menthol, vanillin, peppermint, lemon, mint, strawberry, banana, pineapple, orange and raspberry.

13. A process for the preparation of soft pastilles; said process comprising the following steps:
   a. introducing accurately weighed plasticizer selected from the group consisting of glycerine, sorbitol and combinations thereof and water in a reactor followed by addition of gelling agent selected from the group consisting of gelatin, carrageenan and mixtures thereof and releasing agent selected from the group consisting of lecithin, oil, starch and combinations thereof to form a first mixture wherein a ratio of the gelling agent to the plasticizer is in a range of about 1:2.7 to about 1:3;

b. adding Nicotine active selected from the group consisting of nicotine polacrilex, tobacco plant extract containing nicotine, nicotine oil, nicotine salts, nicotine cation exchanger, nicotine inclusion complex, nicotine bound to cellulose or starch micro-spheres, and combinations thereof to the mixture and mixing for about 30 to about 45 minutes at 1500 rpm to form a second mixture;

c. incorporating adequate quantities of sweetener, flavouring agent, colour and preservative into the second mixture to obtain a mass;

d. collecting the mass in a container followed by cooling and solidification;

e. transferring the solidified mass into a melter to obtain a melted mass; and f. passing the melted mass through an injector into the preformed cavities followed by cooling and blister packaging.

* * * * *